(12) United States Patent
Buttz

(10) Patent No.: US 6,187,764 B1
(45) Date of Patent: Feb. 13, 2001

(54) A AND D VITAMINS AND THEIR METABOLITES: A NEW TREATMENT FOR SEASONAL ALLERGIC RHINITIS AND ATOPY

(76) Inventor: Angelina Pinal Buttz, 7736 Iroquois Dr., El Paso, TX (US) 79912

( * ) Notice: Under 35 U.S.C. 154(b), the term of this patent shall be extended for 0 days.

(21) Appl. No.: 09/241,277

(22) Filed: Feb. 1, 1999

Related U.S. Application Data

(63) Continuation-in-part of application No. 08/850,478, filed on May 5, 1997, now abandoned.

(51) Int. Cl.⁷ .............................. A01N 45/00; A01N 31/04
(52) U.S. Cl. .......................... 514/168; 514/167; 514/725
(58) Field of Search ..................................... 424/406, 408, 424/450, 451, 464; 426/73; 514/168, 167, 725

(56) References Cited

U.S. PATENT DOCUMENTS

| | | |
|---|---|---|
| 4,341,774 * | 7/1982 | Aoki et al. . |
| 4,749,710 * | 6/1988 | Truitt et al. . |
| 5,128,141 * | 7/1992 | Grimberg . |
| 5,135,918 * | 8/1992 | Peraita . |
| 5,510,111 * | 4/1996 | Grimberg . |

FOREIGN PATENT DOCUMENTS

| | | |
|---|---|---|
| 10087495 * | 4/1998 | (JP) . |
| 410087495 * | 4/1998 | (JP) . |
| 10114658 * | 5/1998 | (JP) . |

OTHER PUBLICATIONS

U.S. Food and Drug Administration, Reference Daily Intakes, 1968.*

* cited by examiner

Primary Examiner—Thurman K. Page
Assistant Examiner—Brian K. Seidleck
(74) Attorney, Agent, or Firm—Benjamin Aaron Adler

(57) ABSTRACT

The present invention discloses a method of treating seasonal allergic rhinitis by administering retinol and ergocalciferol to individuals suffering from a hypersensitive immunological response to an allergen. Permanent, long-term relief and prevention of the recurring symptoms of seasonal allergic rhinitis is provided by the dosages and treatment regimens described herein.

10 Claims, No Drawings

A AND D VITAMINS AND THEIR METABOLITES: A NEW TREATMENT FOR SEASONAL ALLERGIC RHINITIS AND ATOPY

CROSS-REFERENCE TO RELATED APPLICATIONS

This application is a continuation-in-part of U.S. Ser. No. 08/850,478, filed May 5, 1997, now abandoned.

BACKGROUND OF THE INVENTION

1. Field of the Invention

The present invention relates generally to the field of immunology. More specifically, the present invention relates to seasonal allergic rhinitis and the use of vitamins A and D for treatment of seasonal allergic rhinitis.

2. Description of the Related Art

Seasonal allergic rhinitis (SAR), commonly called hay fever, is a disease which was first described in ninth century Islamic and sixteenth century European texts. In Europe, the first case of hay fever was reported in 1595 (Emanuel, 1988). The actual cause of the symptoms in individual predisposed to hay fever was not suspected until 1833. That pollen plant was the sole cause of hay fever was proven experimentally in England in 1877. At about the same time, the pollen of *Ambrosia artemisiaefolia,* or common ragweed, was found to be the most active pollen which produced hay fever in America.

Seasonal allergic rhinitis has now reached epidemic proportions. At the end of the nineteenth century in the United States alone, fifty thousand in a population of fifty million inhabitants suffer from seasonal allergic rhinitis. It is now the most common immunologic disorder in humans. Nearly one fifth of the inhabitants of the temperate zone are afflicted. Seasonal allergic rhinitis affects ten percent of children and twenty percent of adolescents and adults. The usual age of onset is between five and ten years and peaks between ten and twenty with males more often affected than females (Emanuel, M. B. Clinical Allergy, 18:295–304, 1988). In 1975, the United States National Health Survey reported twenty-eight million restricted days and two million lost school days per year attributable to allergic rhinitis. Medical costs per year exceeded one billion dollars. With an increasing population and the rising costs of health care, it has become imperative to find an alternative approach for the treatment and prevention of seasonal allergic rhinitis.

Seasonal allergic rhinitis involves both genetic and environmental factors. In the hypersensitivity reaction of susceptible individuals to pollen exposure, the B cell lymphocytes produce large amounts of IgE antibody molecules. These molecules attach themselves to basophils and to mast cells in the tissues near the capillaries. This binding sensitizes the cells to the antigen. When contact is made again with the allergen, the cells respond with the characteristic hypersensitivity reaction. The response causes irritating and painful symptoms, including sneezing, runny nose, itchy eyes, nose and palate, nasal congestion, airway resistance, post-nasal drip, cough, loss of hearing and smell, headache, fatigue and depression.

Medical management of the symptomatology of seasonal allergic rhinitis is based upon pharmacological therapy, immunotherapy and surgical intervention. Pharmacological treatment of seasonal allergic rhinitis currently involves the use of vasoconstrictors, decongestants, corticosteroids, cromolyn sodium and ipratropium bromide. These medications are either prescribed alone or in combination. When pharmacotherapy fails, immunotherapy using pollen extracts is employed, and finally, surgery is undertaken in intractable cases. However, immunotherapy is controversial due to associated fatalities, and surgery entails high morbidity and unpredictable outcomes.

Vitamins are organic compounds which are required by living organisms for maintaining health and were discovered in the early part of the twentieth century in various foods. They were classified according to their solubility's as water-soluble or fat-soluble and named after the letters of the alphabet according to their chronological discovery. Vitamins act as co-factors for different enzymes, which otherwise could not function.

The role of vitamins in relation to classic deficiency diseases is well documented. Beriberi is a thiamine (B1) deficiency first described by the Chinese over 4000 years ago and results in peripheral nervous system disfunction. Scurvy is a deficiency in vitamin C and has been mentioned in medical writings since before 1500 B.C. The symptoms include fatigue, irritability, bleeding and inflamed gums, loosening of teeth, bruising and hemorrhaging. Vitamin D deficiency produces rickets, which is a bone condition resulting in bowed limbs. Vitamin A was the first vitamin to be discovered and deficiencies result in night-blindness. In summary, deficiencies of the water-soluble B complex vitamins and vitamin C cause mainly anemia, nervous system disorders and skin and mucous membrane abnormalities, while deficiencies in the fat-soluble vitamins cause physiological problems including visual impairments, bone abnormalities, blood disorders and fetal death. In all cases, the corresponding pathological condition can be reversed by vitamin supplementation.

It is now believed that vitamins play an important role in the immune system. Cell-mediated immune responses and the role of vitamins as antioxidants and free-radical scavengers has been studied and it is now accepted that vitamin deficiencies affect host defenses. The relationship between vitamins and systemic disorders such as cancer and autoimmune diseases is now better understood. The role of vitamins in humoral responses is currently being studied and evidence suggests that vitamins play a role as immunoregulators. Likewise, substances which require vitamins for their biosynthesis also may exert immunomodulatory influences (DeSimone, 1982).

The prior art is deficient in an effective, inexpensive, curative and preventative treatment for seasonal allergic rhinitis, an atopic disease. The present invention fulfills this long-standing need and desire in the art.

SUMMARY OF THE INVENTION

The present invention describes a method of treatment comprising a combination of vitamin A and D derivatives, specifically retinol and ergocalciferol, to reduce or eliminate the hypersensitive immunological response to allergen exposure that results in seasonal allergic rhinitis.

One object of the present invention is to provide for a curative and preventative treatment for seasonal allergic rhinitis.

In an embodiment of the present invention, there is provided a method of treating or preventing the recurrence of seasonal allergic rhinitis in an individual to thereby reduce or eliminate the hypersensitive immunological response to allergen exposure, comprising the step of administering to the individual a therapeutically effective amount of retinol and ergocalciferol.

In another embodiment of the present invention, there is provided a method of treating or preventing the recurrence of seasonal allergic rhinitis in an individual to thereby reduce or eliminate the hypersensitive immunological response to allergen exposure, comprising the step of: administering to the individual an effective amount of retinol and ergocalciferol, wherein the retinol is administered in an amount of at least 12,000 IU and the ergocalciferol is administered in an amount of at least 60,000 IU, wherein the amount of retinol and the amount of ergocalciferol are administered orally once every 14 days to an individual weighing less than 175 pounds for a period that generally should not exceed 6 consecutive months, wherein the amount of retinol and the amount of ergocalciferol are administered orally once every 10 days to an individual weighing over 175 pounds for a period that generally should not exceed 6 consecutive months.

In yet another embodiment of the present invention, there is provided a method of treating or preventing the reoccurrence of seasonal allergic rhinitis in an individual to thereby reduce or eliminate the hypersensitive immunological response to allergen exposure, comprising the step of: administering to the individual an effective amount of retinol and ergocalciferol, wherein the retinol is administered in an amount of at least 200,000 IU and the ergocalciferol is administered in an amount of at least 300,000 IU, wherein the amount of retinol and the amount of ergocalciferol are administered orally in multiple doses for a period that generally should not exceed 6 consecutive months.

Other and further aspects, features, and advantages of the present invention will be apparent from the following description of the presently preferred embodiments of the invention. These embodiments are given for the purpose of disclosure.

DETAILED DESCRIPTION OF THE INVENTION

No preventative or definite long-term treatment exists for patients with seasonal allergic rhinitis. Medical treatment currently aims at managing the symptoms of the disease with the use of vasoconstrictors, decongestants, antihistamines, corticosteroids, cromolyn sodium, ipratropiumbromide, immunotherapy and surgery.

The present invention describes a method of treatment comprising a combination of vitamin A and D derivatives, specifically retinol and ergocalciferol, to reduce or eliminate the hypersensitive immunological response to allergen exposure that ultimately results in seasonal allergic rhinitis.

The present invention is directed towards a curative and preventative treatment for seasonal allergic rhinitis.

The present invention is directed towards a method of treating or preventing the recurrence of seasonal allergic rhinitis in an individual to thereby reduce or eliminate the hypersensitive immunological response to allergen exposure, comprising the step of: administering to the individual a therapeutically effective amount of retinol and ergocalciferol. Preferably, the retinol and the ergocalciferol are administered in a retinol:ergocalciferol ratio of not less than about 1:1.5 and not greater than about 1:5. Representative methods of administration are orally, parenterally and systemically. A preferred single dose of the retinol is from at least 10,000 IU to 200,000 IU and a preferred single dose of the ergocalciferol is from at least 50,000 IU to 300,000 IU. Generally, the single dose of retinol and the single dose ergocalciferol are administered multiple times for a period of time not to exceed about 6 consecutive months, preferably once every 10 days, once every 14 days, once every two months or once every three months.

The present invention is further directed towards a method of treating or preventing the recurrence of seasonal allergic rhinitis in an individual to thereby reduce or eliminate the hypersensitive immunological response to allergen exposure, comprising the step of: administering to the individual an effective amount of retinol and ergocalciferol. Typically, the retinol is administered in an amount of at least 12,000 IU and the ergocalciferol is administered in an amount of at least 60,000 IU. Generally, the amount of retinol and the amount of ergocalciferol are administered orally once every 14 days to an individual weighing less than 175 pounds for a period not to exceed 6 consecutive months, or once every 10 days to an individual weighing over 175 pounds for a period not to exceed 6 consecutive months. This method may further comprise the step of: orally administering a single dose comprising at least 12,000 IU retinol and at least 60,000 IU ergocalciferol to the individual to thereby reduce or eliminate any residual hypersensitive immunological response to the allergen. Alternatively, the retinol is administered in an amount of at least 200,000 IU and the ergocalciferol is administered in an amount of at least 300,000 IU. In this case, the amount of retinol and the amount of ergocalciferol are administered orally in multiple doses, generally two or three doses, for a period not to exceed 6 consecutive months.

It is specifically contemplated that pharmaceutical compositions may be prepared using the novel vitamin composition of the present invention. In such a case, the pharmaceutical composition comprises the novel vitamin composition of the present invention and a pharmaceutically acceptable carrier. A person having ordinary skill in this art would readily be able to determine, without undue experimentation, the appropriate dosages and routes of administration of this vitamin composition of the present invention. When used in vivo for therapy, the vitamin composition of the present invention is administered to the patient or an animal in therapeutically effective amounts, i.e., amounts that eliminate or reduce seasonal allergic rhinitis. It will normally be administered orally or parenterally, preferably intravenously, but other routes of administration will be used as appropriate. The optimal dose and dosage regimen is set out herein. The schedule will be continued to optimize effectiveness while balanced against negative effects of treatment. See Remington's Pharmaceutical Science, 17th Ed. (1990) Mark Publishing Co., Easton, Pa.; and Goodman and Gilman's: *The Pharmacological Basis of Therapeutics* 8th Ed (1990) Pergamon Press; which are incorporated herein by reference. For oral administration, the vitamin composition will typically be formulated in a unit dosage form (capsule, caplet, tablet, etc.). For parenteral administration, the vitamin composition will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives.

The following examples are given for the purpose of illustrating various embodiments of the invention and are not meant to limit the present invention in any fashion:

EXAMPLE 1

Case # 1:

Demographics: 23 year old Hispanic male.

Medical History re Allergies: Subject developed seasonal allergies 5 years ago; Subject visited an allergist but no allergy tests were performed.

Symptoms: yearly during the Spring and Fall and consisting of runny nose, watery eyes, sneezing and itchy nose and eyes.

Medication(s) Previously Used to Treat Allergies: Ephedrin and prescription nose drops.

Experimental Treatment and Results: Subject was treated in the Spring of 1998 with a total of 900,000 UI oral ergocalciferol and 600,000 UI oral retinol in three divided doses. Subject remained symptom-free during the 1998 Fall allergy season.

EXAMPLE 2

Case # 2:

Demographics: 56 year old Caucasian female, 168 pounds.

Medical History re Allergies: Subject has had seasonal allergies since 1972; Subject has tested positive for allergies to grass, mites, dust and weeds.

Symptoms: yearly during the Spring, Summer and Fall and consisting of severe runny nose, sneezing and watery itchy eyes and nose.

Medication(s) Previously Used to Treat Allergies: over-the-counter allergy medication and an inhaler (during allergy season for allergy-induced asthma).

Experimental Treatment and Results: Subject was treated with a total of 720,000 UI oral ergocalciferol and 144,000 UI oral retinol in twelve divided doses. Subject has remained symptom-free for the past two years.

EXAMPLE 3

Case # 3:

Demographics: 47 year old Caucasian male, 220 pounds.

Medical History re Allergies: Subject has had seasonal allergies and bronchitis since childhood; Subject has tested positive for allergies to weeds.

Symptoms: yearly during the Spring and Fall and consisting of severe runny nose, sneezing, sinusitis and itchy red watery eyes and nose.

Medication(s) Previously Used to Treat Allergies: over-the-counter allergy medication.

Experimental Treatment and Results: Subject was treated with a total of 1,080,000 UI oral ergocalciferol and 216,000 UI oral retinol in eighteen divided doses over a period of six months. Subject has remained essentially symptom-free for years with only occasional symptom reoccurrence in which a single dose of 60,000 UI oral ergocalciferol and 12,000 UI oral retinol relieved symptoms completely.

EXAMPLE 4

Case # 4:

Demographics: 58 year old Hispanic female, 137 pounds.

Medical History re Allergies: Subject has had seasonal allergies since she was 20 years old; Subject tested positive for allergies to weeds, dust and numerous other allergens.

Symptoms: yearly, initially during the Spring and Fall, more recently occurring year-round and consisting of severe sneezing, runny nose, itchy watery eyes and sinisitis.

Medication(s) Previously Used to Treat Allergies: over-the-counter medication (Claritin), corticosteroid injections and immunotherapy.

Experimental Treatment and Results: Subject was treated with a total of 720,000 IU oral ergocalciferol and 144,000 IU oral retinol in divided doses over a period of six months. The severity of subject's symptoms was significantly reduced.

EXAMPLE 5

Case # 5:

Demographics: 58 year old Caucasian male, 200 pounds.

Medical History re Allergies: Subject has had seasonal allergies since childhood.

Symptoms: yearly in the Spring and Fall and consisting of mild runny nose, itchy watery eyes, sneezing and headaches.

Medication(s) Previously Used to Treat Allergies: over-the-counter medication (Benadryl).

Experimental Treatment and Results: Subject was treated with 600,000 UI oral ergocalciferol and 600,000 UI oral retinol in two divided doses. Subject was symptom-free during the 1998 Fall allergy season.

EXAMPLE 6

Case # 6:

Demographics: 51 year old Caucasian male, 210 pounds.

Medical History re Allergies: Subject developed seasonal allergies in his twenties; Subject tested positive for allergies to mesquite, grass and mold Symptoms: yearly, occurring year-round with typical allergy symptoms which have progressively gotten more severe over time.

Medication(s) Used to Treat Allergies: none listed.

Other Pertinent Medical History: Subject is a type II diabetic; Subject is allergic to penicillin.

Experimental Treatment and Results: Subject was treated in the Fall of 1996 with a total of 1,080,000 UI oral ergocalciferol and 216,000 UI oral retinol in divided doses over a period of six months. Subject's symptoms have decreased markedly during the last two years.

EXAMPLE 7

Case # 7:

Demographics: 23 year old Hispanic female, 150 pounds.

Medical History re Allergies: Subject has had seasonal allergy symptoms for the past 10 years.

Symptoms: yearly, worsening in the Spring and Fall and consisting of clear watery nasal discharge and congested nose.

Medication(s) Used to Treat Allergies: none listed.

Experimental Treatment and Results: Subject was treated in the Spring of 1996 with a total of 720,000 UI oral ergocalciferol and 144,000 UI oral retinol in twelve divided doses over a period of six months. Subject has remained symptom-free.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating seasonal allergic rhinitis in an individual to thereby reduce or eliminate the hypersensitive immunological response to allergen exposure, comprising the step of: administering to said individual a therapeutically effective amount of retinol and ergocalciferol wherein a single dose of said retinol is from at least about 10,000 IU to about 200,000 IU and a single dose of said ergocalciferol is from at least about 50,000 IU to about 300,000 IU.

2. The method of claim 1, wherein said retinol and said ergocalciferol are administered in a retinol:ergocalciferol ratio of not less than about 1:1.5 and not greater than about 1:5.

3. The method of claim 1, wherein administration of said retinol and said ergocalciferol is by a route selected from the group consisting of orally, parenterally and systemically.

4. The method of claim 1, wherein said single dose of retinol and said single dose ergocalciferol are administered multiple times.

5. The method of claim 4, wherein said multiple administrations are selected from the group consisting of once every 10 days, once every 14 days, once every two months and once every three months.

6. The method of claim 5, wherein said administration is for a period of time not to exceed about 6 consecutive months.

7. A method of treating seasonal allergic rhinitis in an individual to thereby reduce or eliminate the hypersensitive immunological response to allergen exposure, comprising the step of: administering to said individual an effective amount of retinol and ergocalciferol, wherein said retinol is administered in an amount of at least about 12,000 IU and said ergocalciferol is administered in an amount of at least about 60,000 IU, wherein said amount of retinol and said amount of ergocalciferol are administered orally once every 14 days to an individual weighing less than 175 pounds for a period not to exceed 6 consecutive months, wherein said amount of retinol and said amount of ergocalciferol are administered orally once every 10 days to an individual weighing over 175 pounds for a period not to exceed 6 consecutive months.

8. The method of claim 7, further comprising the step of: orally administering a single dose comprising at least 12,000 IU retinol and at least 60,000 IU ergocalciferol to said individual to thereby reduce or eliminate any residual hypersensitive immunological response to said allergen.

9. A method of treating seasonal allergic rhinitis in an individual to thereby reduce or eliminate the hypersensitive immunological response to allergen exposure, comprising the step of: administering to said individual an effective amount of retinol and ergocalciferol, wherein said retinol is administered in an amount of at least about 200,000 IU and said ergocalciferol is administered in an amount of at least about 300,000 IU, wherein said amount of retinol and said amount of ergocalciferol are administered orally in multiple doses for a period not to exceed 6 consecutive months.

10. The method of claim 9, wherein the number of said multiple doses are selected from the group consisting of two doses and three doses.

* * * * *